United States Patent [19]

Covain

[11] Patent Number: 5,178,833

[45] Date of Patent: Jan. 12, 1993

[54] DEVICE FOR AUTOMATICALLY ANALYZING SAMPLES BY MEANS OF COLORIMETRIC PROCEDURE ESPECIALLY APPLIED TO BLOOD ANALYSIS

[75] Inventor: Serge A. Covain, Baillet, France

[73] Assignee: Biosema, Levallois, France

[21] Appl. No.: 416,261

[22] Filed: Oct. 3, 1989

[30] Foreign Application Priority Data

Oct. 3, 1988 [FR] France .................. 88 12889

[51] Int. Cl.[5] .................. G01N 21/01; G01N 21/11
[52] U.S. Cl. .................. 422/64; 422/63; 422/100
[58] Field of Search .................. 422/63, 64, 100

[56] References Cited

U.S. PATENT DOCUMENTS

| Re. 31,150 | 2/1983 | Ginsberg et al. .......... 422/64 |
|---|---|---|
| 3,788,816 | 1/1974 | Rohrbaugh et al. .......... 422/64 |
| 3,992,631 | 11/1976 | Harte .......... 436/172 |
| 4,052,161 | 10/1977 | Atwood et al. .......... 436/34 |
| 4,170,625 | 10/1979 | Welch . |
| 4,210,724 | 7/1980 | Sogi et al. .......... 422/64 X |
| 4,276,260 | 6/1981 | Drbal et al. .......... 422/64 X |
| 4,287,155 | 9/1981 | Tersteeg et al. .......... 422/64 |
| 4,311,667 | 1/1982 | Gocho .......... 422/64 |
| 4,548,907 | 10/1985 | Seitz et al. .......... 422/82.07 X |
| 4,713,974 | 12/1987 | Stone .......... 422/64 X |
| 4,808,380 | 2/1989 | Minekane .......... 422/64 |

FOREIGN PATENT DOCUMENTS

| 0136002 | 4/1985 | European Pat. Off. . |
|---|---|---|
| 0216026 | 4/1987 | European Pat. Off. . |
| 58-219456 | 12/1983 | Japan . |
| 62-228935 | 10/1987 | Japan . |
| 2083616 | 3/1982 | United Kingdom . |
| WO8200361 | 2/1982 | World Int. Prop. O. . |

Primary Examiner—James C. Housel
Assistant Examiner—Arlen Soderquist
Attorney, Agent, or Firm—Jacobson, Price, Holman & Stern

[57] ABSTRACT

A device for automatically analyzing samples by a colorimetric procedure may be particularly used for blood analysis. A reaction ring bearing at its periphery an array of transparent reaction cups is stationary. An optical fiber is mounted on a rotating disk, concentric with the reaction ring and downwardly oriented with respect to the top of a cup, the optical fiber having one end at a central location where it receives light from a stationary light source and its other end opposite a bottom of a reaction cup in alignment with a measuring photomultiplier.

14 Claims, 7 Drawing Sheets

DEVICE FOR AUTOMATICALLY ANALYZING SAMPLES BY MEANS OF COLORIMETRIC PROCEDURE ESPECIALLY APPLIED TO BLOOD ANALYSIS

FIELD OF THE INVENTION

The invention relates to an automatic analysis device for samples such as blood samples, and more precisely to a rotating device for colorimetric detection which rotates with respect to a stationary ring which constitutes the reaction plate.

BACKGROUND OF THE INVENTION

In the biochemical field, to ensure the continuous metering of blood contents, it is known to use a sample analyzer which comprises three main members. First, there is a rotating plate which bears the blood samples and has at its periphery a plurality of cells intended to receive the blood tubes, said tubes being identified and marked according to the number and kind of analyses that are to be undergone. Beside said first plate, which bears the samples another rotating plate is located which is Finally, a third plate which also rotates is provided at its periphery with transparent cups intended to receive a dosed mixture of blood and reagent. These three plates are advantageously located to define a triangle therebetween so that one or more rotating arms, which each bear a sampling tube, can take a blood sample from a specific cell on the first plate, and then a reagent sample from a flask of the second plate, whereupon said samples are consecutively placed into one of said cups on the rotating plate after the latter has been pivoted up to be located opposite the conveying arm, a washing unit for the sampling tubes being obviously provided between each sampling procedure. When the filling of the cup with said mixture has been completed, the reaction between both components may be carried out and after a certain period of time the mixture can be subjected to a colorimetric analysis This third plate is then moved, by means of a stepwise motor, to locate the cup to be metered opposite a tungsten-halogen lamp which, by means of filters and lenses, projects a suitable light beam onto the cup. The beam horizontally crosses the sample and strikes a metering photosensor which is stationarily mounted at the center area of the reaction plate. The plate is also called a "disposable" plate because after completion of the cup filling and the analysis, the plate is merely taken off the device and replaced by a new plate, the cups of which are ready to undergo a new filling procedure.

This requirement of wholly replacing the disposable plate is a great drawback since the device is non-operable during a substantial period of time which can extend beyond fifteen minutes. This non-operable state is due, on the one hand, to the proper period of time required for replacing the plate, to the zero-point correction thereof and to the restoration of connections, and is also due, on the other hand, to the fact that, after the first cups have been filled again, the first measurement can only be carried out upon completion of the reactions, which are not instantaneously effected. Further, when all the cups are filled, all the reactions must be completed to complete the last analysis. This disadvantage is particularly marked when an urgent analysis is required during the non-operable period of time since it is not then possible to carry the analysis out immediately, before another one, as the device cannot be operated.

Further, the plurality of rotating plates requires the use of a number of driving and locating systems and a sampling arm having a long extension to feed the three plates, or several arms each intended for conveying between two adjacent plates. This results in an analyzing device which is bulky and cumbersome.

It has been proposed to replace the reaction plate by a drawer like device, each drawer consisting of a number of cups, the drawers located beside each other or one on top of each other and able to slide with respect to each other by means of translation motion along rectangular position data. ,Thus a set of cups in a drawer could be replaced without interrupting the reactions in operations carried out in the other drawers However, such a system, although attractive, could not readily be applied as the mechanisms which ensure the motions of the various movable members are complicated. Further, these drawer plates are not well adapted to the thermostatic conditions required in the vessels for receiving the mixture

SUMMARY OF THE INVENTION

It is the applicant's proposal to provide a device for analyzing samples by means of a colorimetric procedure, said device obviating the aforesaid disadvantages of the known apparatus while, on the contrary, enabling analyses to be carried out by a continuous operation with increased speed and accuracy, due to the device having smaller overall external dimensions.

A main object of the present invention is to provide a device for automatically analyzing samples by means of colorimetric procedure, especially adapted to blood analysis, and comprising a sample supporting plate, a reaction ring provided at its peripheray with a plurality of cells able to support transparent reaction cups intended to receive a mixture of sample and reagent to be analyzed, another plate which bears reagent flasks, a system for taking and supplying the sample and reagent into the reaction cups, said system consisting of rotating and/or linking arms which bear sampling tubes, and a colorimetric analysis assembly involving especially a light source, colored filters and a photomultiplier for measuring the light beam which has passed through the reaction cups, said analyzing device being characterized in that the reaction ring which bears at its periphery the array of transparent cups is stationary, whereas the photomultiplier is mounted on a rotating disk which is concentric to the reaction ring, and is downwardly oriented in the direction of the top of the cells, said disk also bearing at least one optical fiber located between a central portion where it receives light from a stationary light source and a peripheral position at which its other end terminates opposite the cup bottom, in alignment with the photomultiplier. Means are provided for continuously ensuring, by using at least two sampling tubes independently operated, the taking of the sample and reagent and the supplying thereof to the reaction cups.

According to a special feature of the invention, the reaction ring is formed by joining three ring sectors which are shaped as removable drawers which can be spaced apart each other.

Advatnageously, a stationary basket or plate which serves as a support for a plurality of reagent flasks is located at the center of the stationary reaction ring, the flasks being regularly and concentrically arranged within the basket around a centpal cylindrical vessel which constitutes a washing station.

According to the invention, the optical fiber mounted on the rotating disk includes a branch in the direction of the reference photomultiplier, said branch being either stationary or also mounted on said rotating disk.

According to the invention, it is also provided that the rotating disk comprises a circular vertical rim extended by a peripheral horizontal flange on which is mounted the metering photomultiplier, the optical fiber terminating in a housing which is externally secured to the circular vertical rim.

The rotating disk is rigidly fixed to a driving ring which is actuated by a motor via transmission belts and at least one reduction ring. The rotating disk includes a central plate which is provided with a through-bore and rigidly secured to the driving ring which is itself provided with a central well through which passes the optical fiber which extends up to the lower portion of the driving ring.

Advantageously, the end of the optical fiber terminates in a housing which is externally secured to the vertical rim, and is upwardly oriented in the direction of the outlet optical lenses.

According to another main feature of the invention, the operating mechanism of the sampling tubes comprises a stationary vertical pole, a support which vertically slides along said pole, and at least one sampling tube mounted at each end of the rotating arm.

More precisely, the sliding motion of the support on guides rigidly fixed to the pole is ensured by means of a vertical threaded rod which is rotatably driven by means of a motor, while cooperating with a tapped portion provided within the base of the support.

The rotating arm, which is rigidly fixed to a central sleeve, is supported beneath an end of the support and is rotatably driven by means of a motor via driving belts and at least one reduction gear.

Further, two motors affixed below the rotating arm each rotatably drive a taking arm, each arm bearing two sampling tubes, around axes located at each end of the rotating arm.

Other advantages and particular features of the invention will become apparent on reading the following description of non-limiting embodiments, with reference to the accompanying drawings.

DETAILED DESCRIPTION OF THE INVENTION

Figure 1:
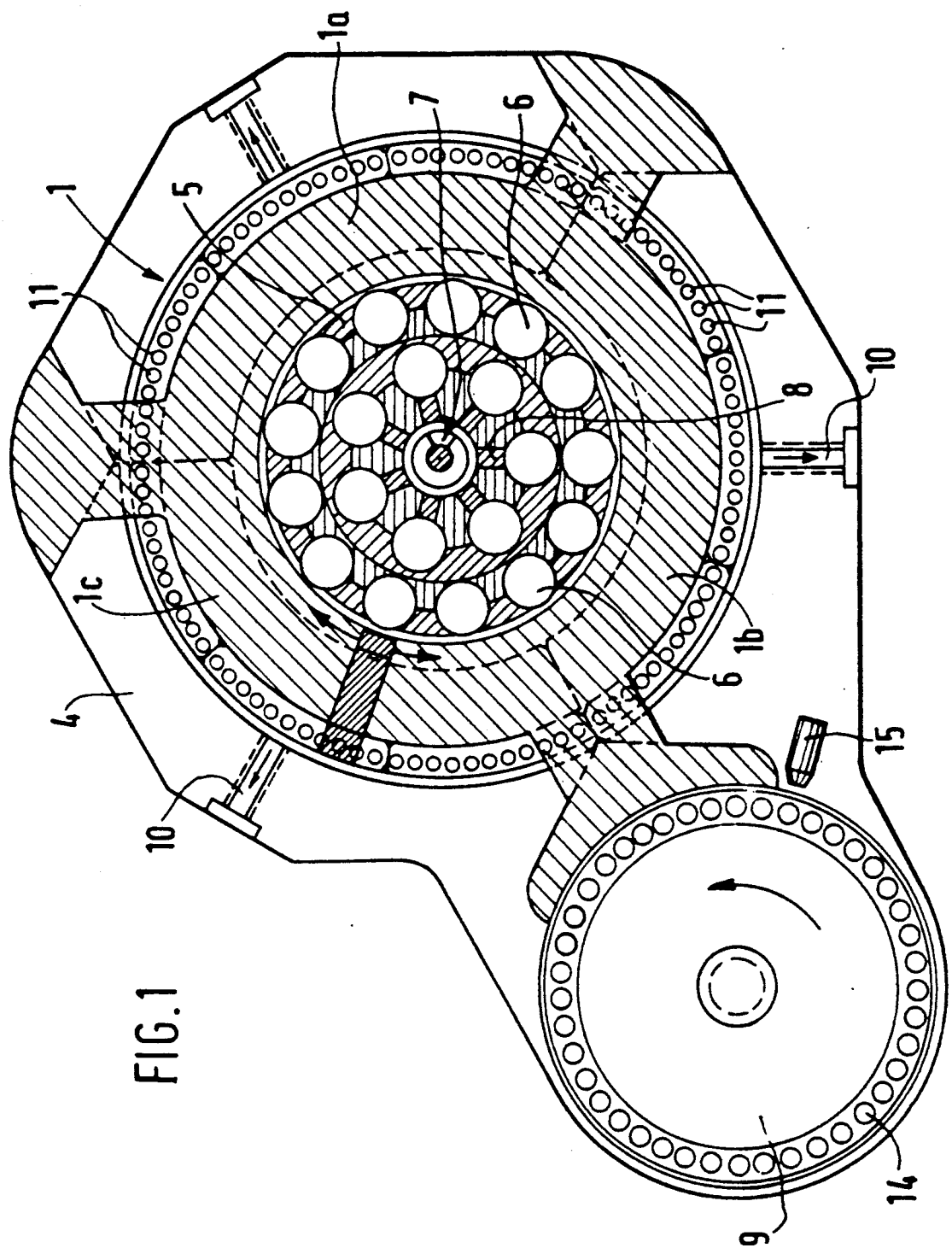
FIG. 1 is a diagrammatic plan view of an analyzing device.
Figure 2:
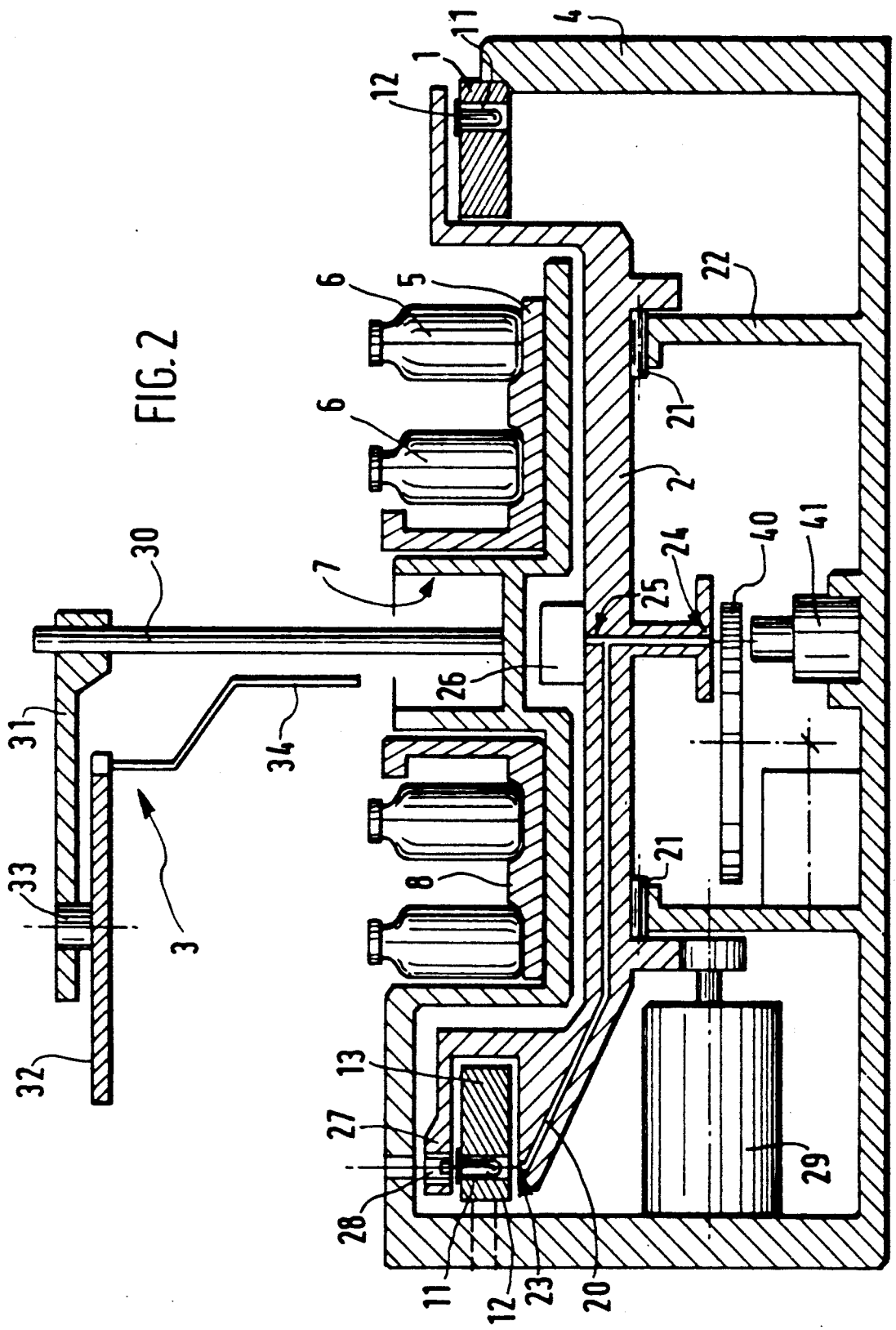
FIG. 2 is a diagrammatic cross-sectional view of the analyzing device.
Figure 3:
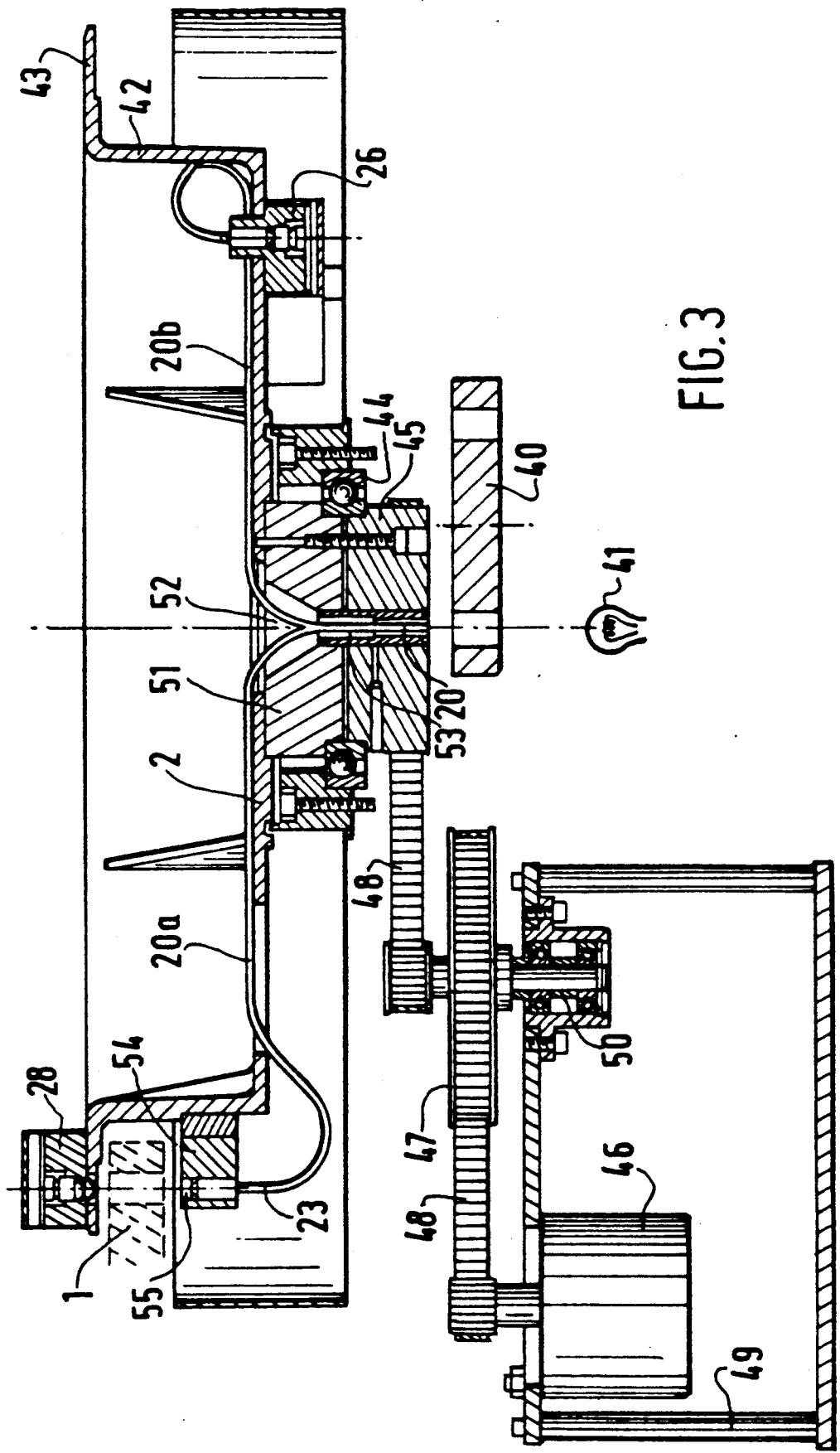
FIG. 3 is a cross-sectional view of the rotating disk provided with an optical fiber.

A device for automatically analyzing samples is shown in FIGS. 1 and 2, wherein the main constituent members of the device are diagrammatically shown so that the main features and the operation thereof can be understood. Certain further embodiments will be explained in more detail with reference to FIGS. 3 to 6.

A stationary supporting base 4 which constitutes the baseplate of the analyzer bears a stationary reaction ring 1, which is formed by joining three ring sectors 1a, 1b and 1c designed as removable drawers, each drawer being independently spaced apart from the adjacent drawers while sliding on a skid 10. The ring 1 is provided at its periphery with an array of wells 11 located beside each other in which can be set small reaction cups 12 having a transparent bottom extending up to the level of the well base. Further, a thermostat 13 which is located on the ring, adjacent the wells, enables the reaction cups 12 to be kept at constant temperature. The central portion of support 4, at the central area of stationary ring 1, comprises a basket or plate 5 which acts as a support for two concentric circular arrays of reagent flasks 6 regularly arranged around a central cylindrical vessel 7 constituting a washing station for the sampling tubes, as hereinafter described. The flasks 6 are arranged on the plate 5 using sets of wedges or struts 8. Thus, the reaction ring 1 and the plate 5 for reagents are both stationary and coaxially located on the same support. It has to be noted that the ring could be dismounted sector by sector by releasing a drawer 1a, 1b or 1c, both remaining drawers being kept in place during the replacement of the first drawer. Flasks 6 may easily be approached from the top. Besides the assembly consisting of the ring 1 and the central plate 5, there is located a rotating plate 9 (as shown in FIG. 1) intended to receive the sampling tubes to be analyzed and provided with peripheral cells 14 in which the tubes are accommodated. This sample storing plate rotates stepwise and enables each tube to be positioned opposite the sampling device A bar-code reader 15 which is located closely adjacent to cells 14 enables information to be read, collected and transferred to the registering-controlling block of the analyzer.

Referring to FIG. 2, there is shown within the support 4, beneath upper plate 5, a rotating disk 2 on which or into which is mounted an optical fiber 20. The disk rotates on rollers 21 mounted on top of supports 22. Optical fiber 20 extends up under wells 11 of ring 1 One end 23 of optical fiber 20 terminates just opposite the bottom of wells 11 of said ring. Its opposite end 24 is located at the disk central area and terminates downwards in the direction of a tungsten-halogen lamp 41 emitting a light beam in the direction of the end 24 of the fiber, while passing through a wheel 40 provided with colored filters. At the central area of disk 2, optical fiber 20 comprises a branch 25 in the direction of a reference photomultiplier 26. At the end of disk 2, on an overhang 27 thereof, a metering photomultiplier 28 is mounted. The metering photomultiplier 28 is located perpendicular to well 11 of ring 1. Disk 2 is rotated by means of a driving motor 29. At the upper part of FIG. 2, there is also shown the operation mechanism 3 for the sampling tubes. This mechanism substantially comprises a central vertical stationary pole 30 along which vertically slides a support 31. The support accommodates a rotating arm 32 having a central rotation axis 33, each end of said arm bearing at least one sampling tube 34. It is understood that, due to the rotating motion of the support in combination with that of the arm, the sampling tubes are able to supply the reagent flasks 6, the reaction cups 12, the sampling tubes on the storing plate 9 and the washing station 7.

With reference to simplified FIGS. 1 and 2, an operating embodiment for the analyzer is described. The embodiment is of simplified form.

The peripheral cells 14 of rotating plate 9 are provided with tubes containing samples to be analyzed. After having read a tube by means of bar-code reader 15, which records the analysis to be carried out, the mechanism 3 is so controlled as to take from the tube a small amount of sample. The lifting of support 31 along pole 30 enables a sampling tube 34 to be released from washing station 7. By means of a combined rotating motion of support 31 and rotating arm 32, followed by a downward motion of the support, sampling tube 34 enters the relative tube, takes therefrom a small amount of sample which, by a reverse motion is fed into a reaction cup 12 which is available on ring 1. The sampling tube 34 is then subjected to washing at station 7 and is then moved again by means of mechanism 3 in the direction of plate 5 where a small amount of reagent is taken from a flask 6. The latter is then put into cup 12 including the sample previously taken, with which it is mixed; the reaction between the sample and the reagent starts in this tube. The filling procedure is continued from another tube to another reaction cup and so one. Simultaneously, the reading of cups which have been previously filled, is made. To this end, the disk 2 is rotatably moved stepwise until the metering photomultiplier 28 and the end 23 of optical fiber 20 are located in perpendicular relationship to the relative cup 12. The light emission from lamp 41 is transmitted after having passed through the desired filter, the filtering wheel 40, via fiber 20 up to cell 23 having a transparent bottom, and the cclorimetric measurement is made by means of the photomutiplier 28. Upon completion of the measurement, the rotating disk is moved by means of motor 29 toward another reaction cup to allow a new measurement to be made. The photomultiplier can sequentially scan the whole reaction ring 1. As soon as a drawer 1a, 1b or 1c on the ring has been measured, it may be released, unloaded of its used cups and provided with empty cups, and then returned to its place on the ring. During this period of time, the measurement and/or filling of both the remaining drawers can be continued without any interruption.

The rotating optical fiber assembly 2 is shown diagrammatically in FIG. 2. There is shown in more detail in FIGS. 3 and 4 an advantageous embodiment of this assembly which has special features. The disk or rotating plate 2 has a vertical circular rim 42 extended by a horizonal peripheral flange 43. The central area thereof is rigidly secured to a plate 51 provided with a through-bore 52, which is mounted on bearings 44 and is rotatably driven by means of a driving ring 45 which is itself actuated by a motor 46 through another reduction ring 47 and grooved transmitting belts 48. The motor 46 and the supporting bearing 50 of the intermediate ring 47 are mounted on a stationary base 49. The opening 52 in plate 51 together with a central hole provided on the driving ring 45 form a well 53 for the passage of an optical fiber 20 which extends up to the level of the lower part of said ring. Beneath the latter and opposite the fiber are located the filters of the filter wheel 40, whereas the lamp 41 is still mounted beneath filter wheel 40 in alignment with the well 53.

At the exit of well 53, the optical fiber is divided in two parts 20a and 20b which extend on each side of plate 2. Fiber 20a ends in a housing 54 externally fixed to rim 42 and which enables its end 23 to be located so as to be upwardly oriented in the direction of outlet optical lenses 55. The metering photomultiplier 28 is located above the peripheral flange 43 so that its sensing part is downwardly oriented in the direction of lenses 55. The fiber 20b ends on the opposite side in a reference photomultiplier 26 fixed beneath disk 2 and adjacent the circular rim 42, the spacing between the plate and the gear driving mechanism thereof enabling this member to be positioned.

Figure 4:
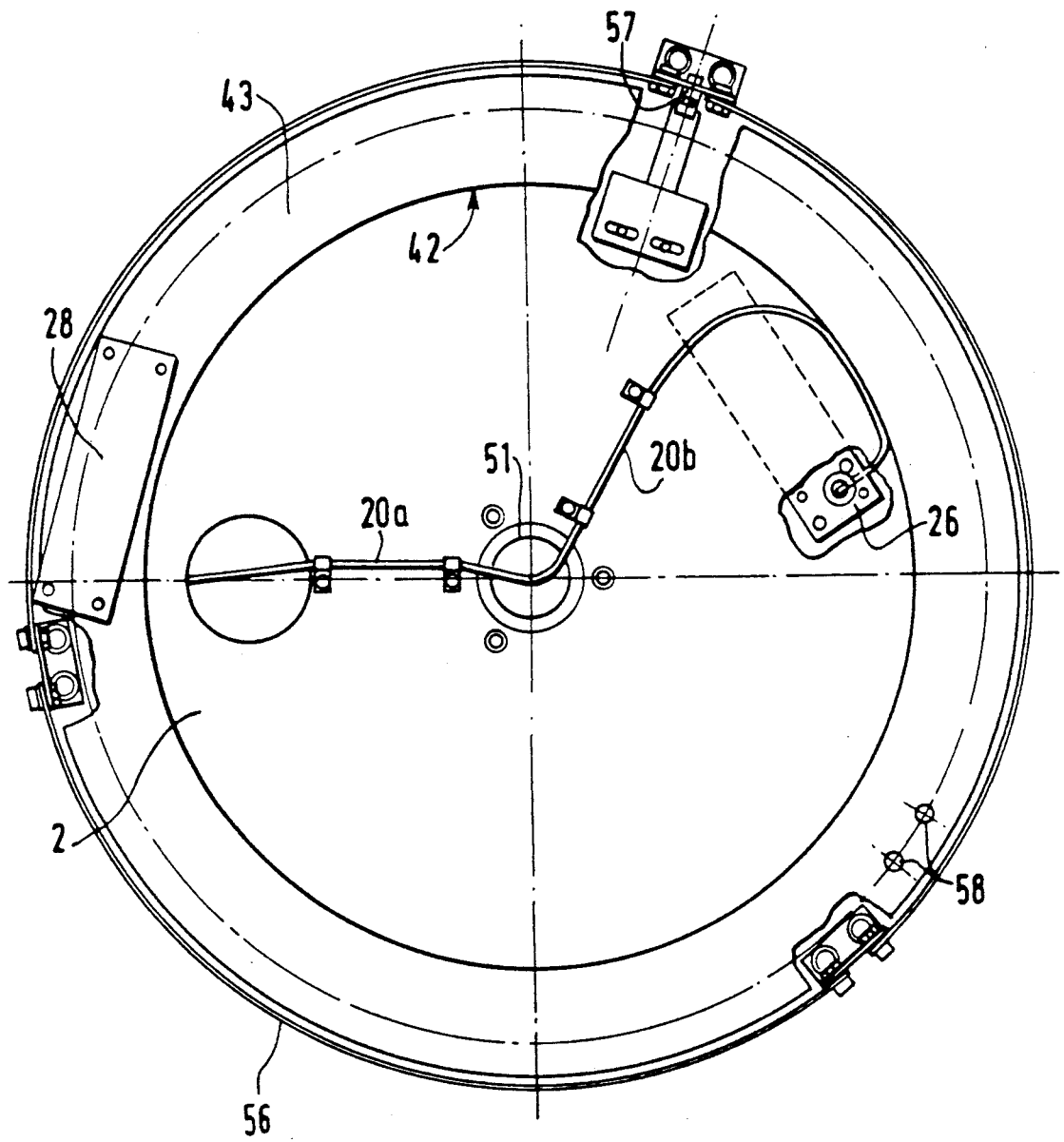
FIG. 4 is a plan view of the rotating disk shown in FIG. 3.

The rotating plate 2 together with its two photomultipliers cover the stationary reaction ring 1 located under the peripheral flange 43. Referring more particularly to FIG. 4, rotating disk 2 is surrounded with a binding edge 56 intended to mask the light in the circular measurement area. An optical fork 57 for detecting the reference position of the plate, and that of the driving stepwise motor, is also provided on the stationary bidning edge. On the periphery of flange 43 are provided two supply holes 58, the purpose of which is hereinafter described.

Figure 5:
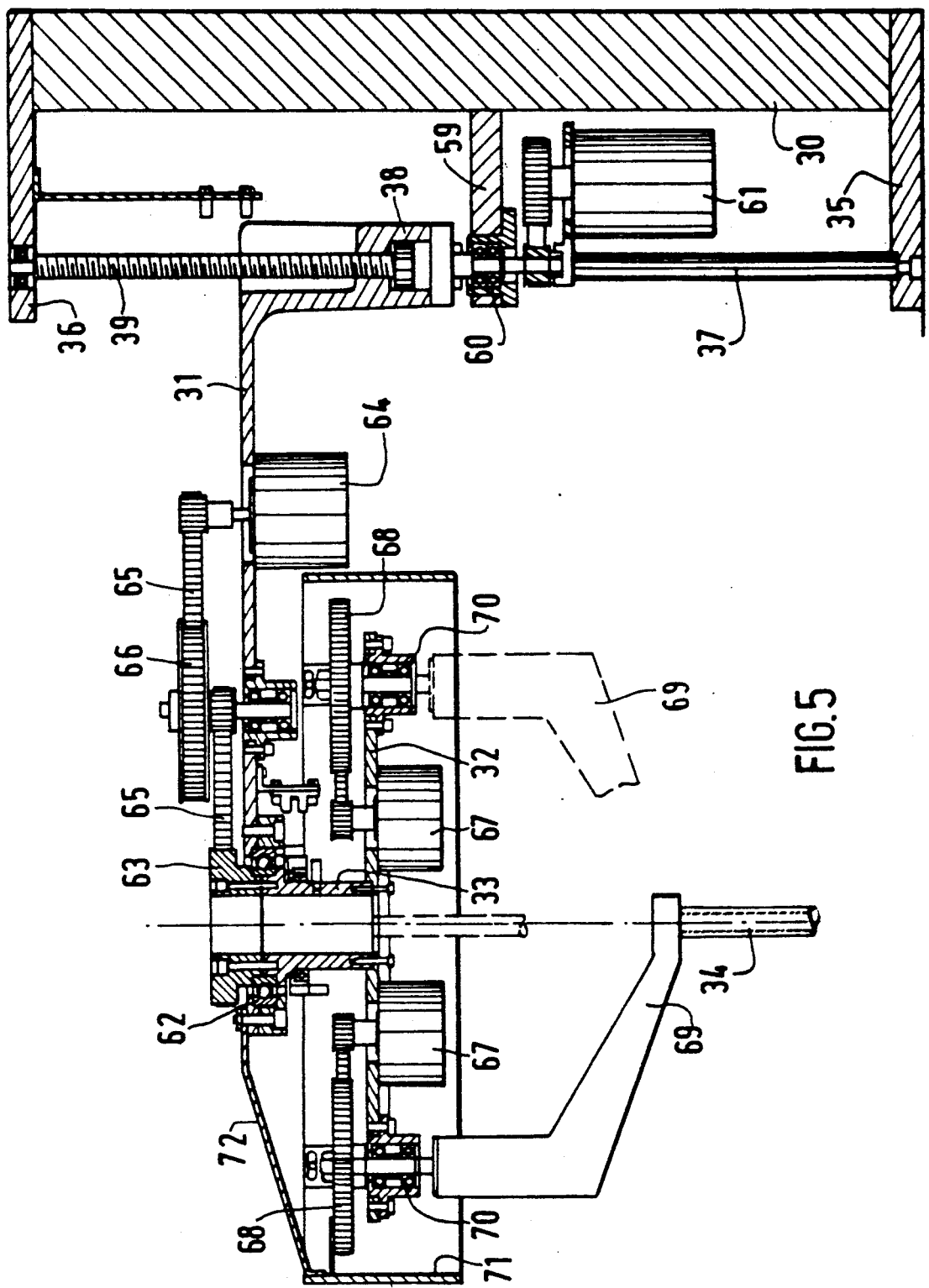
FIG. 5 is a cross-sectional view of the operating mechanism of the sampling tubes.

The operating mechanism of the sampling tubes 3, has been diagrammatically shown in FIG. 2. In FIGS. 5 and 5 there is shown in more detail an advantageous embodiment of this assembly.

Figure 6:
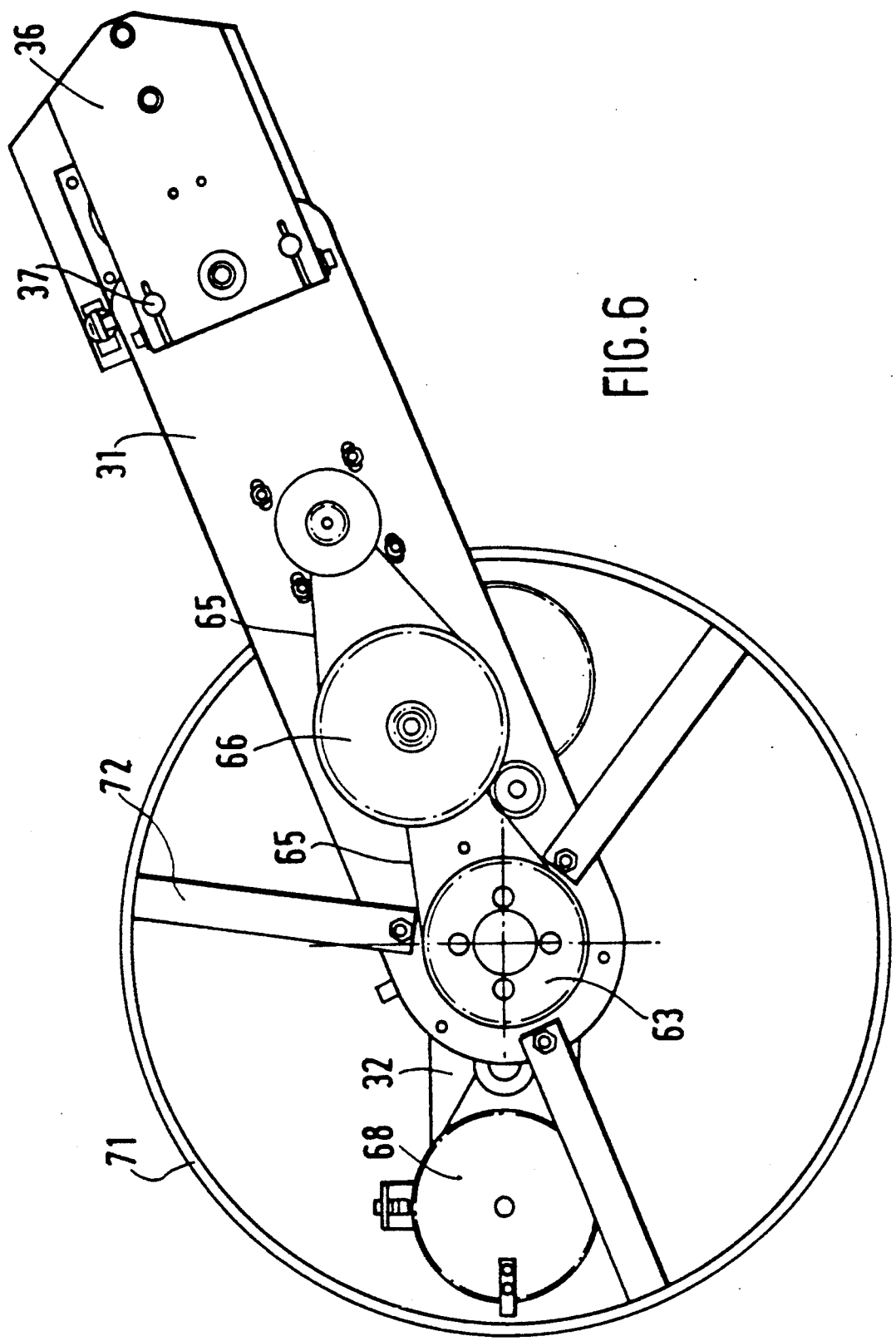
FIG. 6 is a plan view of the operating mechanism shown in FIG. 5.

As shown in FIGS. 5 and 6, the central pole 30 is mounted on a stationary base 35 and is covered by an end plate 36 at the upper part thereof. Between the base and the plate two guiding vertical columns 37 are extended along which base 38 of support 31 is slidably mounted. The threaded rod 39 which is vertically located between the columns 37 is supported by a spacer 59 which is rigidly fixed to pole 30, through bearings 60. The threaded rod is rotatably driven by means of a small motor 61. Its threading cooperates with a screw provided in the base 38 of the support, so that the rotation of rod 39 in any direction enables the support 31, which is slidably mounted on columns 37, to be either lifted or lowered. The support 31 overhangs above and in the direction of the center of the reaction ring. A rotating arm 32 is mounted under the support. The rotating arm is rigidly fixed to a central sleeve 33 which is supported at the end of the support by means of bearings 62. The vertical axis of sleeve 33 is located at right angles to the central area of the reaction ring.

Figure 7:
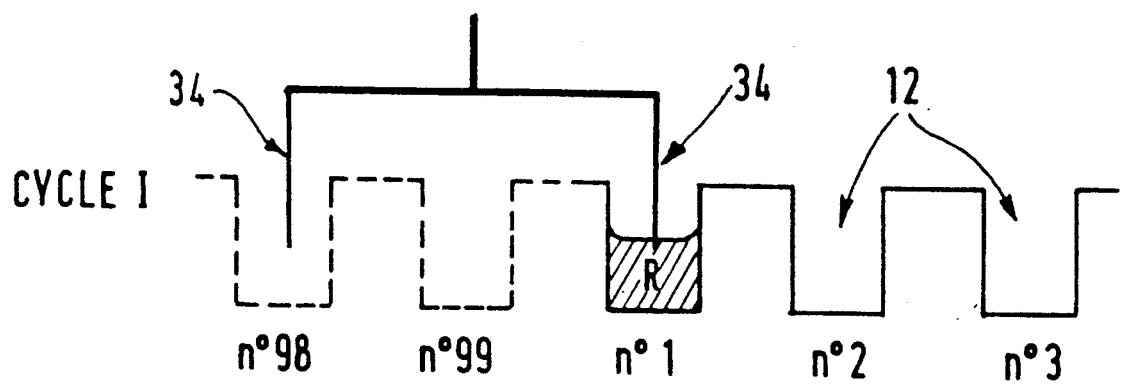
FIGS. 7 to 9 are diagrammatic views showing the various steps of filling the reaction cups.
Figure 8:
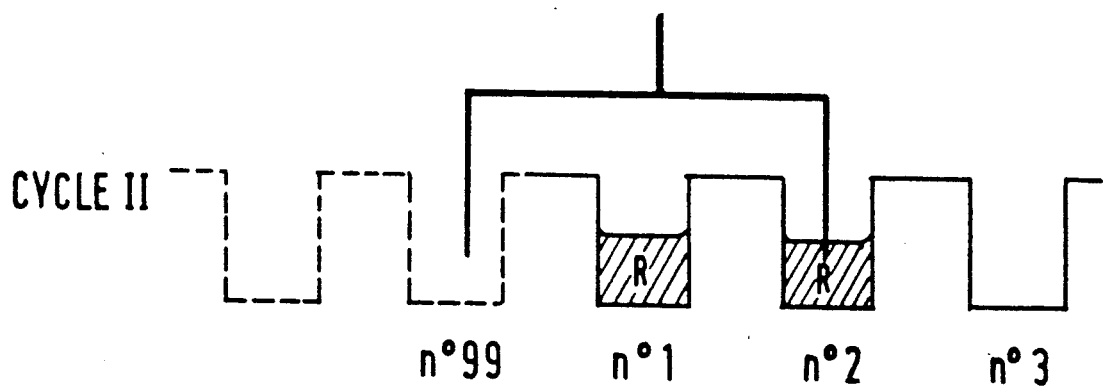
Figure 9:
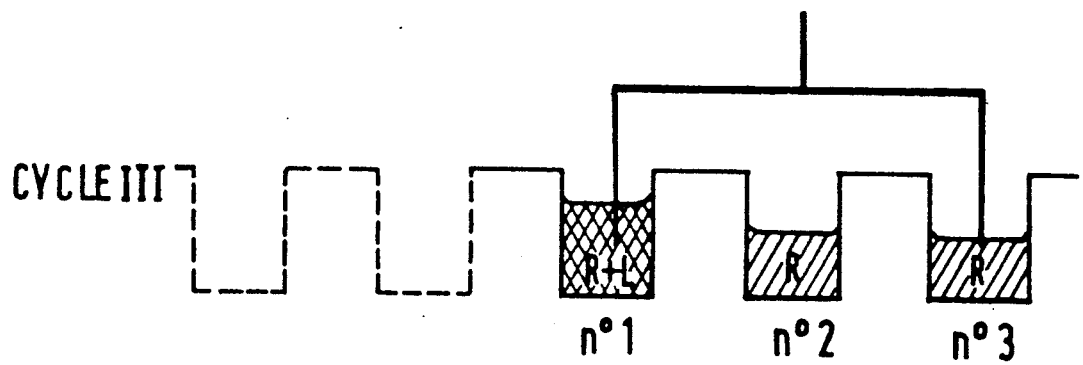

The sleeve is bonded to a grooved driving gear 63 which is rotatably actuated by a motor through transmission belts 65 and another reduction gear 66. Gears 63, 66 and belts 65 are mounted above support 31, whereas the motor 64 is mounted beneath support 31 beneath the rotating arm and the support base 38. Under the rotating arm 32 are located, on each side of sleeve 33, two motors 67 intended to rotatably drive a taking arm 69 through a second driving gear 68. Driving gear 68 is mounted above and at the end of rotating arm 32, and the rotation axis of taking arm 69, which is mounted under the rotating arm, extends the central axis of driving gear 68, a set of bearings 70 being provided at this level. The left portion of FIG. 5 shows that taking arm 69 is bent, the lower end spreading out along a circumference having a radius equal to the gap between sleeve 33 and its driving gear 68. The arm end may be thus placed above the central part of the reaction ring. This end bears two sampling tubes 34 which (see FIG. 7) extend downwardly. The tubes 34 are connected by means of flexible ducts (not shown) which extend along the taking arm 69 and then under the rotating arm 32 and, after passing through hollow sleeve 33, spread out on the support and are connected to suitable suction and ejection systems, such as injection syringes which are not shown.

Thus, the rotating arm 32 is provided at each end thereof with a taking arm 69 whose rotation motion is controlled independently from that of the other arm. Rotating arm 32 is protected by means of a circular covering hood 71 which is supported by fixing lugs 72 mounted on support 31.

There has been described hereinabove, with reference to FIGS. 1 and 2, a simplified operating embodiment of the analyzer. The provision for both taking arms with two sampling tubes, each mounted at the end of a rotating shaft and rotating, as hereinabove described, enables much more favorable operating rates to be used. One of the arms can be in operation, i.e. loading the reaction cups, whereas the other one can be at the washing station.

There is hereinafter described an example of a distribution and reading cycle, wherein use is made of improved systems such as those described with reference to FIGS. 3 to 9.

At the beginning of the handling, the reaction ring, which may support 99 cups arranged on the periphery thereof, is empty. When starting, a taking arm is first moved so that one of the sampling tubes 34 mounted thereto is introduced into a desired reagent (R) flask 6 to suck a small amount therefrom. Then the support is lifted to release the sampling tube from the flask and due to a combined rotation motion of the rotating arm and sampling tube, the latter is moved up to be at right angles to a cup 12 which can be designated as cup 1 on the ring. Reagent is then fed in the cup by lifting support 31, the sampling tube passing through one of both feeding holes 58 as hereinabove stated and terminating just above the cup. The adjacent sampling tube has also entered the adjacent hole 58 at right angles to a cup located two steps farther and which is thus cup 98 (see FIG. 7). It is obvious that at this time the rotatable plate 2 is stationary; it continues its motion only when the sampling tubes are lifted out of holes 58, whereupon the sampling tubes are released from the reaction ring. The first cycle is completed.

The second feeding cycle thus begins. During the transfer of the sampling tubes used in the first cycle to be washing tank, both sampling tubes on the adjacent arm are moved, as in the first cycle, so that one is taking further reagent (R), and the other one is used for supplying cup 1 with sample (L) to be mixed therein with the reagent, the two samplings having been carried out almost simultaneously.

Then, the filing operation is continued in the other cups along subsequent cycles identical to cycle III.

After each reagent/sample supply has been completed, the rotating plate 2 is moved from one gauge and a reading is made by the photomultiplier. After completion of cycle I, it has made a first reading on cup 1 only filled with reagent, that provides a reference value. After completion of cycle II, a first reading on cup 2 is made and a second reading on cup 1, whereby providing a second reference value. After completi-on of cycle III, it ensures a first reading on cup 3 filled with reagent and sample, followed by a second reading on 2 and a third one on 1 and so on.

Thus, there are provided for each cup a plurality of measurements which enable curves to be plotted while taking into account the reaction duration for each mixture, which is different with respect to the reagent used.

The handling of these members is automatically programmed. The device is able to carry out automatically an analysis and a re-analysis of any sample. The device, which is monitored by a number of microprocessors, may embody simultaneous multifunctions and store information and results relative to the patients. The results are advantageously displayed by a printer and provide client identification and detailed results of the analysis.

The invention which has been described by way of an example, is not limited to this embodiment but encompasses all the alternative forms deriving therefrom.

What is claimed is:

1. An analyzer for automatically analyzing samples by means of a colorimetric procedure comprising:
    a sample supporting plate;
    a stationary reaction ring provided at a periphery of said ring with a plurality of cells supporting transparent reaction cups for receiving a mixture of sample and reagent for analysis;
    a stationary reagent plate located concentrically within said stationary reaction ring supporting a plurality of reagent flasks;
    means for taking and supplying tne sample and reagent into said reaction cups;
    wherien said means for taking and supplying comprises a stationary support located at the center of said stationary reagent plate, a rotatable support rotatably attached to said stationary support, an arm rotatably supported beneath an end of said rotatable support on a first axis of rotation, and a sampling arm bearing at least one sampling tube independently rotatably supported at each end of said arm such that the sampling arm rotates about second axes located at each end of said arm with a distal end of each sampling tube being spaced from a respective one of said second axes; and
    a colorimetric analysis assembly;
    wherein the colorimetric analysis assembly comprises a stationary light source for providing light, colored filters, a metering photomultiplier for measuring the light passed through the reaction cups, at least one optical fiber and a rotating disk which is concentric with the stationary reaction ring, said photomultiplier being mounted on said rotating disk in a downwardly oriented direction toward the top of a respective transaprent reaction cup and said at least one optical fiber is mounted on said rotating disk between a central position of said rotating disk where a first end of the at least one optical fiber receives light from the stationary light source and a peripheral position of said rotating disk at which a second end of the at least one optical fiber terminates opposite the bottom of the respective transparent reaction cup.

2. The analyzer according to claim 1, wherein the reaction ring includes three removable ring sectors.

3. The analyzer according to claim 1, wherein reagent flasks are regularly and concentrically arranged on the reagent plate around a wash station which comprises a central cylindrical vessel.

4. The analyzer according to claim 1, wherein the colorimetric analysis assembly further comprises a reference photomultiplier and said at least one optical fiber comprises a branched optical fiber with a third end directed at the reference photomultiplier.

5. The analyzer according to claim 1, wherein the rotating disk comprises a circular vertical rim having a peripheral horizontal flange extending from an upper edge, the metering photomultiplier being mounted on the peripheral horizontal flange and a housing which is externally secured to the circular vertical rim in which the second end of said at least one optical fiber terminates.

6. The analyzer according to claim 5, further comprising optical outlet lenses, wherein the second end of said at least one optical fiber is upwardly oriented toward the bottom of said respective reaction cup such that light from the at least one optical fiber passes through the optical outlet lenses.

7. The analyzer according to claim 1, wherein the rotating disk is rigidly fixed to a driving ring which is actuated by a motor via transmission belts and at least one reduction gear.

8. The analyzer according to claim 1, wherein the rotating disk comprises a central plate which is provided with a through-bore and is rigidly secured to a driving ring having a central well therein though which the at least one optical fiber passes.

9. The analyzer according to claim 1, wherein the rotating disk is surrounded with a stationary binding edge for masking light from the stationary light source.

10. The analyzer according to claim 1, wherein two supply openings are provided in a peripheral horizontal flange of the rotating disk.

11. The analyzer according to claim 1, wherein the stationary support is a stationary vertical pole and the rotatable support is vertically slidable on said stationary vertical pole by means of guides rigidly fixed to said stationary vertical pole, a vertical threaded rod rotatably driven by a motor, and a taped portion provided in the rotatable support which cooperates with the vertical threaded rod.

12. The analyzer according to claim 1, wherein the arm is rotatably driven by a motor via driving belts and at least one reduction gear.

13. The analyzer according to claim 1, wherein each sampling arm supports two of said sampling tubes and is rotatably driven by a motor affixed under the sampling arm.

14. The analyzer according to claim 1, wherein a circular covering hood is mounted on the rotatable support to protect the sampling arm.

* * * * *